United States Patent [19]

Bahrmann et al.

[11] Patent Number: 4,723,047

[45] Date of Patent: Feb. 2, 1988

[54] PROCESS FOR THE PREPARATION OF NONADECANEDIOLS

[75] Inventors: Helmut Bahrmann, Hamminkeln; Boy Cornils, Hofheim; Werner Konkol; Jürgen Weber, both of Oberhausen; Ludger Bexten, Hunxe; Hanswilhelm Bach, Duisburg, all of Fed. Rep. of Germany

[73] Assignee: Ruhrchemie Aktiengesellschaft, Fed. Rep. of Germany

[21] Appl. No.: 910,650

[22] Filed: Sep. 23, 1986

[30] Foreign Application Priority Data

Sep. 26, 1985 [DE] Fed. Rep. of Germany ....... 3534317

[51] Int. Cl.$^4$ .................... C07C 29/14; C07C 29/16; C07C 31/20
[52] U.S. Cl. .................................................. 568/862
[58] Field of Search ............................. 568/862, 883

[56] References Cited

U.S. PATENT DOCUMENTS

| | | | |
|---|---|---|---|
| 3,912,785 | 10/1975 | Suzuki | 568/862 |
| 3,933,920 | 1/1976 | Nienburg et al. | 568/862 |
| 4,079,064 | 3/1978 | Taylor | 568/862 |
| 4,144,191 | 3/1979 | Hartwell et al. | 568/883 |
| 4,215,077 | 7/1980 | Matsumoto et al. | 568/862 |
| 4,216,343 | 8/1980 | Rogier | 568/853 |
| 4,248,802 | 2/1981 | Kuntz | 568/909 |
| 4,263,449 | 4/1981 | Saito et al. | 568/862 |
| 4,275,243 | 6/1981 | Saito et al. | 568/862 |
| 4,329,521 | 5/1982 | Homeier et al. | 568/909 |
| 4,451,680 | 5/1984 | Knifton | 568/909 |

FOREIGN PATENT DOCUMENTS

| | | |
|---|---|---|
| 2410156 | 9/1975 | Fed. Rep. of Germany . |
| 2627354 | 12/1976 | Fed. Rep. of Germany . |
| 2914189 | 10/1980 | Fed. Rep. of Germany . |
| 3017682 | 11/1980 | Fed. Rep. of Germany . |
| 3235030 | 3/1984 | Fed. Rep. of Germany . |

*Primary Examiner*—J. E. Evans
*Attorney, Agent, or Firm*—Jordan B. Bierman

[57] ABSTRACT

The present invention relates to a process for the preparation of nonadecanediols by the hydroformylation of oleyl alcohol. Rhodium and salts of sulfonated or carboxylated triarylphosphines, which are soluble in organic media and insoluble in water, are used as hydroformylation catalysts. The hydroformylation product is then treated with a diluted solution of a base dissolved in water, the aqueous phase separated and the hydroformylation product treated with hydrogen at elevated temperature in the presence of a hydrogenation catalyst.

14 Claims, No Drawings

PROCESS FOR THE PREPARATION OF NONADECANEDIOLS

The present invention relates to a process for the preparation of nonadecanediols by the hydroformylation of oleyl alcohol in the presence of rhodium complex catalysts and hydrogenation of the hydroformylation product after separation of the catalyst.

The preparation of aldehydes and alcohols by the reaction of olefins with carbon monoxide and hydrogen is known. The reaction is catalyzed with hydridometal carbonyls, preferably those of the metals of the 8th group of the periodic system. Apart from cobalt, which finds wide industrial application as a catalyst metal, rhodium has also been gaining in significance over the past few years. In contrast to cobalt, rhodium makes it possible to carry out the reaction at low pressure; moreover in the presence of excess phosphine as a complexing agent, straight-chain n-aldehydes are formed preferably and only a minor amount of iso-aldehydes. Finally, with the use of rhodium catalysts, the hydrogenation of olefins to saturated hydrocarbons is much lower than with the use of cobalt catalysts.

In the commercially established processes, the rhodium catalyst is used in the form of modified hydridorhodium carbonyls which contain additional and, in some cases, excess ligands. Tertiary phophines or phosphites have proved particularly useful as ligands. Their application makes it possible to reduce the reaction pressure to under 30 MPa.

However, with this process, the separation of the reaction products and the recovery of the catalyst homogeneously dissolved in the reaction product causes problems. Generally, the reaction product is distilled out of the reaction mixture. In practice, this route can, however, only be employed for the hydroformylation of lower olefins, i.e. olefins with up to 5 carbon atoms in the molecule, owing to the thermal sensitivity of the aldehydes and alcohols formed.

When long-chain olefins are hydroformylated, products with a high boiling point are formed which cannot be distilled out of the homogeneously dissolved rhodium complex catalyst. The thermal loading of the distillation mixture leads to considerable losses of both valuable products and catalyst, owing to the formation of heavy oil and the decomposition of rhodium complex compounds, respectively.

The thermal separation of the catalyst is avoided by the use of water-soluble catalyst systems. Such catalysts are described, for example, in the DE-PS No. 26 27 354. Here, solubility of the rhodium complex compounds is achieved by the use of sulfonated triarylphosphines as complex components. With this process variant the catalyst is separated from the reaction product after completion of the hydroformylation reaction simply by separation of the aqueous and organic phases; i.e. without distillation and therefore without any additional thermal process steps. Another feature of this method is that n-aldehydes are formed with higher selectivity from terminal olefins and iso-aldehydes only to a very minor extent. Apart from sulfonated triarylphosphines, carboxylated triarylphosphines are also used as complex components of water-soluble rhodium complex compounds.

The use of water-soluble catalysts for the hydroformylation of low olefins, in particular ethylene and propylene, has stood the test excellently. If higher olefins such as hexene, octene or decene are used, the conversion and/or selectivity of the reaction to n-compounds shows a marked decline. Often, the reaction is no longer economic for commercial scale preparation.

A process for the hydroformylation of oleyl alcohol is described in the U.S. Pat. No. 4,216,343. Rhodium is used as a catalyst on a carrier together with excess triphenylphosphite. The reaction of the alcohol with synthesis gas takes place at 130° C. and 7.0 to 7.5 MPa. Triphenylphosphine can also be used instead of triphenylphosphite. The reaction product, formyloctadecanol, is then reacted, without prior catalyst separation, with methanolic formaldehyde solution in the presence of alkali to the geminal bis-(hydroxymethyl)-octadecanols.

Alternatively, the rhodium-containing formyloctadecanol can first be reacted with formaldehyde to the corresponding hydroxymethylformyloctadecanol. Then hydrogenation takes place to the corresponding 9.9(10,10)-bis(hydroxymethyl)octadecanol either with hydrogen in the presence of a copper chromite catalyst or with $LiAlH_4$.

Both routes for the hydrogenation of formyloctadecanol are not satisfactory. The use of an alkaline formaldehyde solution not only leads to an increase in the reaction volume but also to the occurrence of rival reactions and thus to the formation of by-products. $LiAlH_4$ is a very expensive hydrogenation reactant and therefore reduces the economy of the process considerably.

The DE-OS No. 29 14 189 relates to the preparation of nonadecanediols by the hydroformylation of oleyl alcohol and subsequent hydrogenation in one stage. Rhodium in the presence of a very high excess of tertiary amine is employed as a catalyst for both reaction steps. The reaction takes place at a total pressure of 20 MPa (7.5 MPa CO, 12.5 MPa $H_2$) and a temperature rising from 130° C. to 180° C. The diol yield is about 71 to 76% of the theoretical value. The rhodium-containing catalyst remains in the reaction mixture. The cited reference does not go into its separation from the reaction mixture and its reprocessing.

The high reaction temperature leads to a destruction of the catalytically acting rhodium complex. The catalyst is therefore deactivated and cannot be recirculated to the reaction. Moreover, there is a danger of metallic rhodium being deposited in the reactor which can either not be recovered at all or only in a complicated manner.

Therefore, the problem consisted in developing a process which makes it possible to hydroformylate oleyl alcohol in high yields, to separate the catalyst from the hydroformylation product as completely as possible under mild conditions, and to hydrogenate the formyl alcohol formed as an intermediate product to the diol in the conventional manner.

This problem is solved by a process for the preparation of nonadecanediols by the hydroformylation of oleyl alcohol at 100° to 170° C. and 10 to 45 MPa in homogeneous phase and in the presence of a catalyst system containing both rhodium and aromatic phosphines in molar excess related to the rhodium, separation of the catalyst and hydrogenation of the hydroformylation product, characterised in that salts of sulfonated or carboxylated triarylphosphines which are soluble in the organic medium and insoluble in water are used as aromatic phosphines, the hydroformylation product is treated with a diluted aqueous solution of a base, the aqueous phase containing rhodium and phosphine is separated and the hydroformylation product is treated with hydrogen in the presence of a hydrogenation catalyst at elevated temperature.

The procedure according to the invention combines the advantages of the known hydroformylation processes without having their disadvantages. On the one hand, it permits the hydroformylation of oleyl alcohol in homogeneous phase thus ensuring a high conversion. On the other hand, it permits a mild and near complete separation of the catalyst before the hydrogenation of formyloctadecanol to the corresponding diol mixture.

The catalyst system consists of salts of sulfonated or carboxylated triarylphosphines which are soluble in organic media but insoluble in water and of rhodium bound as a complex to the phosphorus atom. The cations of the salts exhibit the groups $[NR_2H_2]^+$ and/or $[NR_3H]^+$ where R denotes alkyl groups with 4 to 12 carbon atoms, aryl or cycloalkyl groups with 6 to 12 carbon atoms.

The salts of the sulfonated or carboxylated triarylphosphines are added in dissolved form to the hydroformylation mixture. However, it is also possible to add them in solid form to the oleyl alcohol used in the hydroformylation and, if necessary, to improve their solubility by the addition of solvents. Suitable solvents include benzene, toluene, xylene and cyclohexane.

Hydroformylation of the oleyl alcohol takes place at 100° to 170° C. and 10 to 45 MPa (100 to 450 bar) in the presence of 30 to 150 ppm rhodium, preferably 50 to 100 ppm rhodium, related to the oleyl alcohol used. The salts of the sulfonated or carboxylated triarylphosphines are employed in a ratio of 5:1 to 200:1, preferably 40:1 to 100:1 (mol triarylphosphine salt per g-atom rhodium). The synthesis gas composition can vary between a $CO:H_2$ ratio of 10:1 to 1:10; it is normally about 1:1.

Mono, di or trisulfonated triphenylphosphine; namely, $(C_6H_5)_2 PC_6H_4SO_3H$, $C_6H_5P(C_6H_4SO_3H)_2$, or $P(C_6H_4SO_3H)_3$, have proved to be particularly useful sulfonated triarylphosphines. Moreover, mixtures of mono, di and trisulfonated triphenylphosphines are also suitable as catalyst components. After the hydroformylation, the reaction mixture is treated with a diluted aqueous solution of a water-soluble alkali.

The water-soluble alkalis required to split salts of sulfonated or carboxylated triarylphosphines which are soluble in organic media but insoluble in water must be sufficiently alkaline to achieve the required pH value with the diluted aqueous solution of the alkali during the extraction of the hydroformylation mixture. This requirement is fulfilled by the alkali and alkaline earth hydroxides, but aqueous tetraalklammonium hydroxide solutions can also be employed. The concentration of the water-soluble base is 0.01 to 10% by weight, preferably 0.5 to 5% by weight, related to the aqueous solution.

When the two phases are mixed at temperatures of $\leq 70°$ C., preferably $\leq 40°$ C., the corresponding secondary or tertiary amines are liberated from the $[NR_2H_2]^+$- or $[NR_3H]^+$; at the same time a water-soluble salt of the sulfonated or carboxylated triarylphosphine is formed. This enters the aqueous phase by extraction and is separated together with the rhodium which is bound as a complex to the phosphorus. During this extraction the pH value of the mixture of the two phases is to be $\geq 8$, preferably $\geq 8.5$. Generally, it is recommended to keep a pH range of 8 to 10, preferably 8.5 to 9.

The extraction is simple to perform. As a result of the reduced thermal loading, the deactivation and thermal decomposition (and thus the damage to the catalyst system) is reduced, and the formation of undesirable by-products arising from the hydroformylation product is also diminished. The recovery rate is unusually high even in the first extraction step and is >90% by weight, based on the rhodium used. This result can be improved by multiple extraction, if desired.

The organic and aqueous phases separate quickly and completely. In order to accelerate the separation of the two phases, a centrifuge can be employed if necessary and the top organic phase can then be separated from the bottom aqueous phase. Coalescing elements are also successfully employed; e.g. Franken filters.

After separation of the aqueous phase containing rhodium and triarylphosphine, the hydroformylation product is washed several times with cold water—if necessary—in order to remove any remaining alkaline substances. The cleaning process must be performed thoroughly in order to avoid alkali-catalyzed secondary reactions, e.g. aldolization during the hydrogenation.

The raw formyl alcohol liberated from the hydroformylation catalyst is hydrogenated at elevated temperature in the presence of a catalyst. Hydrogenation can be carried out in the gaseous phase, in suspension, or in the liquid phase. The catalysts contain copper, copper chromite, cobalt or nickel. Sometimes compounds containing alkaline earth, zinc, aluminum and/or chromium are also present as promoters. They can be pure metal catalysts or can be applied to carrier materials. Carrier catalysts with 25 to 65% by weight metal, preferably 40 to 60% by weight metal, based on the catalyst mass, have proven to be particularly suitable. Pumice stone, siliceous earth, alum earth, aluminum oxide and $SiO_2$ in its various forms find application as carrier materials. A nickel carrier catalyst with 55% by weight nickel and about 30% by weight $SiO_2$, based on the total catalyst mass, has proven to be particularly suitable. Useful solvents for hydrogenation are cyclohexane, methylcyclohexane, methanol, ethanol, 2-ethylhexanol and other higher alcohols. However, the solvent can also be omitted.

Depending on the residence period of the product to be hydrogenated and the type of catalyst used, the temperatures range from 80° to 220° C. With the gas phase operation, the pressure is between about 0.01 and 15 MPa. If the raw product is hydrogenated in the liquid phase, the pressures are correspondingly higher and are 5 to 35 MPa, preferably 10 to 25 MPa.

The reaction period is 1 to 10 hours, preferably 2 to 6 hours, depending on the selected reaction conditions.

Another advantage of the process according to the invention consists in the fact that the active hydroformylation catalyst can be recovered from the aqueous rhodium-containing phase without any great complicated apparatus. The extract is acidified with e.g. mineral acids up to a pH value of about 1 and the aqueous phase is extracted with a secondary or tertiary amine dissolved in an organic solvent (e.g. benzene or toluene) in accordance with the aforementioned composition. Thereby, the originally used amine salt of the sulfonated or carboxylated triarylphosphine is regenerated. As it is not soluble in water, it is transferred together with the complex-bound rhodium to the organic phase. The re-extract recovered in this manner can find application directly as a hydroformylation catalyst. If necessary, the rhodium and/or the phosphorus (III) ligands can be topped up.

The invention is described in detail in the following examples. In the following, the abbreviations mean:
TPPDS: triphenylphosphinedisulfonic acid salt
TPPTS: triphenylphosphinetrisulfonic acid salt
TPPODS: triphenylphosphine oxide disulfonic acid salt
TPPOTS: triphenylphosphine oxide trisulfonic acid salt
TPPSTS: triphenylphosphine sulfide trisulfonic acid salt.

EXPERIMENT 1

Preparation of triisooctylammonium salt from TPPTS (phosphine mixtures I and II)

The sulfonation of triphenylphosphine with oleum and its subsequent further processing is described in DE No. 32 35 030 A1. On the basis of this procedure, triphenylphosphine is reacted with oleum at room temperature and the resultant mixture is hydrolyzed by the addition of cold water (see table 1, column 1). Subsequently, a solution of triisooctylamine in toluene is added and the mixture is stirred for about 30 minutes. After completion of the stirring, the lower aqueous phase containing sulfuric acid is separated. Adjustment of the pH value to 4.6 is made by the addition of a 3% aqueous sodium hydroxide solution and the aqueous phase is separated and discarded. Then the toluene solution is washed another two times with water. The work takes place under the strict exclusion of oxygen to avoid undesirable oxidation of the phosphine. The two phosphine mixtures I and II are prepared in this way. Their analytical data are compiled in Table 1.

TABLE 1

| (Values determined as sodium salts by means of the HPLC analysis) | | | |
|---|---|---|---|
| | sulfonation[1] raw product | phosphine[2] mixture I | phosphine[2] mixture II |
| TTPDS | 0.441 weight % | 1.714 weight % | 0.74 weight % |
| TPPTS | 2.58 weight % | 8.087 weight % | 5.01 weight % |
| TPPODS | 0.048 weight % | 0.205 weight % | 0.42 weight % |
| TPPOTS | 0.578 weight % | 0.809 weight % | 1.20 weight % |
| P(III)[3] | 0.055 mol | 0.165 mol/kg | 0.105 mol/kg |

[1] aqueous sulfuric acid solution
[2] amine salt solution in toluene
[3] determined iodometrically

EXPERIMENT 2

Preparation of tri-(di-2-ethylhexylammonium) salt of TPPTS (phosphine mixture III)

5130 g of a triphenylphosphine sulfonation mixture which has already been hydrolyzed with cold water (for composition refer to Table 1: sulfonation raw product) are mixed with 212 g (0.876 mol) di-(2-ethylhexyl) amine dissolved in 848 g of toluene in a $N_2$ atmosphere at 20° C. The mixture is stirred for two hours and left to stand overnight. Three phases form, the upper phase (438 g) consists of toluene, the middle phase (742 g) contains the amine salt of TPPTS. Its P(III) content is 0.342 mol/kg (determined iodometrically).

The lower phase (5113 g) contains water and sulfuric acid.

EXPERIMENT 3

Preparation of tri-(di-n-hexylammonium) salt of TPPTS (phosphine mixture IV)

1273 g of the hydrolysis mixture employed in Experiment 1 are mixed with 38.9 g (210 mmol) of dihexylamine dissolved in 156 g of toluene in a $N_2$ atmosphere at 20° C. The mixture is stirred for two hours and left to stand overnight. Three phases form. The upper phase (101 g) consists of toluene, the middle phase (120 g) contains the dihexylamine salt of di or trisulfophenylphosphine dissolved in toluene, while the lower phase (1229 g) only contains aqueous sulfuric acid and is separated. Treatment of the toluene solution of the amine salt with an aqueous sodium hydroxide solution (adjustment of the pH value) is dispensed with. The pH value of the solution is around 1. Its P(III) content is 0.121 mol/kg.

EXAMPLE 1

Preparation of nonadecanediol from oleyl alcohol (a) Hydroformylation of oley alcohol 519 g of HD-Ocenol 80/85 (product of Henkel; 63% by weight oleyl alcohol), 80 g of the phosphine mixture I and 25 mg of rhodium in the form of Rh(III)-2-ethylhexanoate are placed in a 2 liter autoclave which is provided with a rotary stirrer. The hydroformylation is carried out in a protective nitrogen atmosphere. The pressure (27 MPa) is set with synthesis gas ($CO/H_2 = 1:1$). The reaction period is 6 hours at 130° C.; the synthesis gas consumed during the reaction is replaced by fresh gas under pressure. Then the autoclave is cooled, depressurised and the reaction product examined with a gas chromatograph. 0.5% by weight of the oleyl alcohol remain unreacted.

(b) Separation of the rhodium catalyst 247 g of the hydroformylation product formed under a) are fed into a three-neck flask and intensively stirred. Then an 8% aqueous sodium hydroxide solution (9 ml) is added and the pH adjusted to 8.9. In order to accelerate the separation of the two phases, the mixture is centrifuged for 5 minutes in a laboratory centrifuge (4500 rpm). Two phases are formed; the bottom aqueous phase containing an insoluble sediment.

In the upper, organic phase (235.3 g), there is only 3.8% by weight of the rhodium originally contained in the hydroformylation mixture but, in the bottom phase (10.34 g), 94.8% by weight is present and, in the insoluble residue (0.55 g), 1.4% by weight is found.

(c) Hydrogenation of the hydroformylation product

The hydroformylation product obtained in accordance with b) and free of rhodium and P(III) ligand is hydrogenated in the presence of a nickel carrier catalyst which has 55% by weight Ni and about 30% by weight $SiO_2$, based on the total catalyst mass. 5% by weight nickel catalyst based on the organic material employed is used, the pressure is 10 MPa, the temperature 150° C., and the reaction period 2 hours. The autoclave employed has a stirring means and has a volume of 1 liter. The gas chromatographic analyses and the feed, intermediate and final products are compiled in the following table.

TABLE 2

| Feed product: HD-Ocenol 80/85 | weight % | Hydroformylation product | weight % | Hydrogenation product | weight % |
|---|---|---|---|---|---|
| First runnings | 1.66 | $C_{12}$—$C_{15}$—alcohols | 4.2 | | |
| $C_{10}$—$C_{15}$ alcohols | 4.31 | | | n-$C_{14}$—alcohol | 2.4 |

TABLE 2-continued

| Feed product: HD-Ocenol 80/85 | weight % | Hydroformylation product | weight % | Hydrogenation product | weight % |
| --- | --- | --- | --- | --- | --- |
| n-$C_{16}$ alcohol | 9.15 | n-$C_{16}$—alcohol | 10.54 | n-$C_{16}$—alcohol | 12.7 |
| unsaturated $C_{16}$—alcohols | 5.13 | $C_{17}$— + isomeric $C_{18}$—alcohols | 2.12 | second runnings: | 2.6 |
| Second runnings: | 1.74 | second runnings: | 5.9 | n-$C_{17}$—alcohol + triisooctylamine | 6.1 |
| n-$C_{18}$—alcohol | 5.15 | n-$C_{18}$—alcohol | 7.0 | n-$C_{18}$—alcohol + triisooctylamine | 10.7 |
| n-$C_{18}$—alcohol singly unsaturated | 62.69 | formyl-n-$C_{18}$—alcohol | 55.4 | $C_{19}$—diol | 62.7 |
| n-$C_{18}$—alcohols multiply unsaturated | 8.55 | other formyl alcohols | 4.81 | other diols + triols | 2.8 |
| n-$C_{20}$—alcohol | 1.55 | elutable last runnings | 0.2 | | |
| $C_{22}$—alcohol | 0.07 | triisooctylamine | 9.8 | | |

*all values determined with a gaschromatograph (d) Distillation work-up of the hydrogenated product mixture 112 g of the hydrogenated product mixture obtained in accordance with (c) are freed from the catalyst residue by filtration and distilled in a simple distillation apparatus (10 cm long Vigreux column) at a pressure of 0.39 kPa. The first fraction passes over at 73° to 203° C. It contains toluene, lower alcohols and triisooctylamine.

The main fraction (63 g), which passes over at 203° to 220° C., exhibits a nonadecanediol content of 84.4% by weight based on the main fraction. The percentage of higher boilers (heavy oil) is 10.7% by weight (based on the product used).

(EXAMPLE 2)

Preparation of nonadecanediol from oleyl alcohol (a) Hydroformylation of oleyl alcohol 273 g of HD-ocenol 80/85, 126.5 g of the phosphine mixture (II) (corresponding to 13.3 mmol P(III)) and 27 g of rhodium in the form of Rh(III) 2-ethylhexanoate are placed in a 1 liter autoclave and hydroformylated in the manner described in Example 1. After 6 hours the oleyl alcohol has been completely reacted.

(b) Separation of the rhodium catalyst (comparative test)

The hydroformylation product is treated with aqueous sodium hydroxide solution as described under Example 1(b) but the pH value is adjusted to 7. The consequence is a greatly reduced separation of the rhodium from the organic phase. The amount of rhodium present in the aqueous phase is only 14.7% by weight of the feed amount. This shows that a pH value of above 7 must be set to ensure sufficient separation of the rhodium from the organic phase. The hydroformylation product liberated from the aqueous phase is hydrogenated as described under 1(c). It has a nonadecanediol content of 47.9% by weight.

In the same manner as in Example 1(d), 154 g of the hydrogenated raw mixture are placed in a simple distillation apparatus (10 cm long Vigreux column) and distilled at 0.26 kPa. After the first fraction has been removed, 18 g of the second fraction, exhibiting a nonadecanediol content of 71.7%, pass over. 51 g of product with a nonadecanediol content of 85.0% by weight are isolated as the main fraction. The percentage of higher boilers (heavy oil) is about 9% by weight, based on to the feed product, and thus is only slightly less than in Example 1(d).

EXAMPLE 3

Preparation of nonadecanediol from oleyl alcohol

The hydroformylation of oleyl alcohol is repeated in accordance with Example 1(a). Instead of HD-Ocenol 80/85, HD-Ocenol 90/95 (product of Henkel; 78.9% by weight oleyl alcohol) is employed. The phosphine mixture I is used as a ligand as stated in Example 1(a).

After separation of the rhodium as described under 1(b), whereby 90% of the employed rhodium passes into the aqueous phase, the hydrofromylation mixture exhibits the following composition: toluene + first fraction constituents 2.5% by weight, hexadecanol 4.1 weight-%, octadecanol 5.2 weight-%, triisooctylamine 12.3 weight-% and 68.6 weight-% formyloctadecanol. After hydrogenation as described under 1(c), a raw product containing 73.3 weight-% nonadecanediol is obtained.

EXAMPLE 4

Preparation of nonadecanediol from oleyl alcohol 600 g HD-Ocenol 90/95, 187 g of phosphine mixture III, and 30 mg of rhodium in the form of Rh(III) 2-ethylhexanoate, as well as 9.3 g of di-2-ethylhexylamine are placed in a 2 liter autoclave which is provided with a rotary stirrer.

Hydroformylation takes place in accordance with Example 1(a). In addition to some components of lower concentration, the hydroformylation mixture contains 7.2 weight-% di-2-ethylhexylamine; 4.6 weight-% hexadecanol; 3.9 weight-% octadecanol; 10.3 weight-% formylhexadecanol and 65.5 weight-% formyloctadecanol. The rhodium is separated in the same manner as described in Example 1(b), whereby 81% by weight of the rhodium employed passes over into the aqueous phase. After hydrogenation, which is carried out in the same manner as described in Example 1(c), a raw product is obtained which exhibits 64.5% by weight nonadecanediol. Example 4 proves that hydroformylation is not impaired by the presence of free amine and that there is no increase in the formation of higher boiling substances.

EXAMPLE 5

Preparation of nonadecanediol from oleyl alcohol 600 g HD-Ocenol 90/95, 99.2 g of the phosphine mixture IV, and 30 mg of rhodium in the form of Rh(III), are placed in a 1 liter autoclave and hydroformylated in accordance with Example 1(a). However, no conversion takes place; the mixture removed from the autoclave exhibits a pH value of 1.2. The mixture removed from the autoclave had its pH value adjusted to 4.7, under stirring with aqueous sodium hydroxide.

The aqueous phase was separated and the remaining organic phase was hydroformylated in accordance with Example 1(a). Conversion takes place immediately. After the reaction has been completed, the hydroformylation raw product exhibits a content of 73% by weight formyloctanol. After hydrogenation in the manner described under Example 1(c) a raw product with the following composition is obtained:

3.5% by weight hexadecanol; 5.9% by weight octadecanol; 72.3% by weight nonadecanediol and 9.5% by weight higher boilers.

Through the alkalization it was possible to pass 99% by weight of the rhodium into the aqueous phase.

Example 5 proves that the hydroformylation depends on the pH value which should be greater than 1.2, if possible, 4.5 to 5.0. Therefore, it is to be recommended that the phosphine mixture serving as a ligand should be adjusted to this level.

What we claim is:

1. A process for the preparation of nonadecanediols by the hydroformylation of oleyl alcohol in a homogeneous organic phase and in the presence of a catalyst system containing both rhodium and aromatic triaryl phosphine salts in molar excess based on said rhodium, said salts being of sulfonated or carboxylated phosphines and in said organic phase and insoluble in water, treating the reaction mixture with a dilute aqueous solution of a base whereby a water soluble salt of the sulfonated or carboxylated triaryl phosphine is formed and an organic layer and an aqueous layer are formed, the water soluble salt of the sulfonated or carboxylated triaryl phosphine entering the aqueous layer together with the rhodium which is bound as a complex to the phosphorous, separating the organic layer containing the hydroformylation product and hydrogenating it in the presence of a hydrogenation catalyst at an elevated temperature.

2. The process of claim 1 wherein said insoluble salts contain $[NR_2H_2]^+$ and/or $[NR_3H]^+$ as cations, wherein R is an alkyl group having 4 to 12 carbon atoms, or aryl or cycloalkyl having 6 to 12 carbon atoms.

3. The process of claim 1 wherein said hydroformylation is carried out at 100° C. to 170° C. and 10 to 45 MPa.

4. The process of claim 1 wherein said system comprises 30 to 150 ppm rhodium, based on said oleyl alcohol, and the molar ratio of said salts to said rhodium is 5:1 to 200:1.

5. The process of claim 4 wherein said system comprises 50 to 150 ppm rhodium and said molar ratio is 40:1 to 100:1.

6. The process of claim 1 wherein treatment with aqueous base takes place at a temperature of 70° C. or less and a pH of more than 8.

7. The process of claim 6 wherein said temperature is 40° C. or less and said pH is at least 8.5.

8. The process of claim 1 wherein said hydrogenation catalyst contains nickel, cobalt, or copper, and said hydrogenation is carried out at 80° to 220° C. and 0.01 to 35 MPa.

9. The process of claim 8 wherein said hydrogenation catalyst contains nickel and a carrier, and said hydrogenation is carried out at 80° to 160° C. and 10 to 25 MPa.

10. The process of claim 1 wherein said triarylphosphines comprise mono, di, or trisulfonated triphenyl phosphine.

11. The process of claim 1 wherein said triarylphosphines are a mixture of mono, di, and triphenyl phosphines.

12. The process of claim 1 wherein said base is alkali metal hydroxide, alkaline earth hydroxide, or an aqueous tetra-alkylammonium hydroxide solution.

13. The process of claim 1 wherein said base is 0.01 to 10% by weight of said solution.

14. The process of claim 13 wherein said base is 0.5 to 5% by weight of said solution.

* * * * *